United States Patent [19]

Malmros et al.

[11] Patent Number: 5,372,801
[45] Date of Patent: Dec. 13, 1994

[54] BIOLOGICAL STAIN COMPOSITION, METHOD OF PREPARATION AND METHOD OF USE FOR DELINEATION OF EPITHELIAL CANCER

[75] Inventors: Mark K. Malmros, Newton; Raymond J. Tucci, Yardley; Pier J. Cipriani, Newtown, all of Pa.

[73] Assignee: CTM Associates, Inc., Newtown, Pa.

[21] Appl. No.: 67,506

[22] Filed: Jun. 7, 1993

Related U.S. Application Data

[63] Continuation-in-part of Ser. No. 785,520, Oct. 31, 1991, abandoned.

[51] Int. Cl.⁵ ............................................. A61K 31/54
[52] U.S. Cl. .................... 424/7.1; 514/226.2; 544/37
[58] Field of Search .............. 424/7.1, 9; 514/226.2; 206/569; 544/37

[56] References Cited

U.S. PATENT DOCUMENTS

| | | | |
|---|---|---|---|
| 3,743,088 | 7/1973 | Henkin | 206/12 |
| 4,181,128 | 1/1980 | Swartz | 128/207.21 |
| 4,321,251 | 3/1982 | Mashberg | 424/3 |
| 4,977,177 | 12/1990 | Bommer et al. | 514/410 |
| 5,018,531 | 5/1991 | Hartman | 128/774 |
| 5,069,754 | 12/1991 | Watanabe et al. | 162/168.2 |

OTHER PUBLICATIONS

Remington Pharmaceutical Sciences (1975) Ed: Hoover, John E., pp. 1368, 1369, & 1413–1418.

*Primary Examiner*—Gary E. Hollinden
*Attorney, Agent, or Firm*—William H. Drummond

[57] ABSTRACT

A biological stain composition contains toluidine blue O and a pharmaceutically acceptable oxidizing agent to convert any leuco toluidine blue O to the chromo form. A dry composition for preparing the stain includes the toluidine blue O, the oxidizing agent and an effervescent agent. These compositions are preferably buffered to improve shelf stability and clinical consistency. Compositions for intra-oral application contain a flavoring agent.

10 Claims, No Drawings

BIOLOGICAL STAIN COMPOSITION, METHOD OF PREPARATION AND METHOD OF USE FOR DELINEATION OF EPITHELIAL CANCER

This application is a continuation of our PCT International Application PCT/US92/08722, filed Oct. 7, 1992, which was, in turn, a continuation-in-part of our U.S. application Ser. No. 07/785,520, filed Oct. 31, 1991, now abandoned.

This invention relates to biological stain compositions and methods of preparing and using such compositions.

More specifically, the invention concerns an improved biological stain composition, method of preparation and method of use for in situ delineation of epithelial cancer.

In a further and more specific respect the invention concerns compositions and methods of preparation and use in which the specificity of biological stain tests for epithelial cancer is improved by reducing incidental staining of non-cancerous tissue, thereby reducing the number of false positives.

In another respect the invention relates to biological stain compositions having improved chemical stability, and, thus, having improved clinical consistency and shelf-life.

In still another and more specific respect, the invention pertains to biological stain compositions for use in detecting oral epithelial cancer, which have improved flavor and, thus, are more palatable to the patient.

Toluidine blue 0, also known as tolonium chloride, is a basic dye of the thiazine group. The use of toluidine blue 0 was reported in 1963 as a clinical stain for the in situ delineation of dysplasia and carcinoma, to assist in the selection of punch biopsies sites in patients suspected of having carcinoma of the uterine cervix. (Richart, Am. J. Obstet. Gyn. 86:703 1963). Thereafter toluidine blue 0 was reported as an in vivo stain for delineation of oral intraepithileal neoplastic changes (Niebel, et al., J. Am. Dent. Assoc. 68:801 1964). Subsequently over two dozen publications have demonstrated the utility of toluidine blue 0 as an in situ stain for the detection and aid in the diagnosis of oral carcinomas. In 1989, Rosenberg, et al. reported a meta-analysis of 16 major clinical studies using toluidine blue 0 for the diagnosis of oral cancer, reporting a sensitivity of 93.5%, with a specificity of 73.3% (Rosenberg et al., Oral Surg, Oral Med, Oral Path, 67:621 1989).

The specificity of the toluidine blue 0 test by the visual determination of dye uptake by specific lesions is reduced by the non-specific staining of mucosal tissue. Such non-specific staining can be limited somewhat by proper decolorization after the stain application, using a 1% acetic acid solution.

The patent to Mashberg, U.S. Pat. No. 4,321,251, issued Mar. 23, 1982, discloses a procedure for reducing false negatives and false positives of the toluidine blue 0 test for malignant lesions of the oral cavity. The Mashberg method utilized a six-step procedure which is repeated after 10-14 days. Each repetition of the procedure involves a pre-rinse with acetic acid, two pre-rinses with water, a rinse with toluidine blue 0 solution, a post-rinse with acetic acid and a post-rinse with water. If a lesion is found in the first repetition, the specific area is restained 10-14 days thereafter and a second positive yields a positive diagnosis.

The relative unwieldy procedures employed by Mashberg and the relatively low specificity of the test of the toluidine blue 0 test if such complicated procedures are not used have severely limited the use of the toluidine blue 0 test for oral cancer. It would be highly advantageous if the specificity of the test could be increased while simultaneously reducing the complexity of the test procedures.

In addition to the unwieldy prior art procedures for using toluidine blue 0 as a biological stain composition, its use in detecting oral cancers has been inhibited by the limited shelf life and the bad taste of the prepared dye compositions. It would be advantageous to provide such compositions which have improved stability, in order to provide longer shelf life and to minimize degradation of flavoring agents in the prepared compositions.

We have now discovered compositions, methods of preparation and methods of use whereby such improvement in the specificity of the toluidine 0 stain test for epithelial cancer is obtained, utilizing, however, simplified procedures for preparing and using the stain composition. Our discovery is based on two principles, namely, that the toluidine blue 0 stain solution should be freshly prepared and/or that any leuco toluidine blue 0 which is present in the stain composition, either introduced therein in the leuco form or formed in situ by reduction of the chromo form, should be oxidized to the chromo form and maintained in the chromo form at the time of application of the stain to the suspected cancerous sites.

We have also discovered that the clinical consistency, shelf-life and flavor of toluidine blue 0 compositions are substantially improved by controlling the pH of the prepared solution with a suitable buffering agent to a pH in the range of from about 3.5 to about 5.0. Such buffered compositions are more clinically consistent in detecting oral cancers, because the staining characteristics of the dye are pH dependent and a buffered stain composition is less affected by minor patient-to-patient variations in saliva pH. Further, degradation of the dye and degradation of flavoring agents, which are normally sensitive to pH effects, are minimized by such buffering.

Preparation of a fresh stain composition is preferably accomplished by dissolving an effervescent tablet, containing an effective preselected quantity of the dye, in a preselected quantity of an aqueous solvent. Conversion of the leuco form of the dye to the chromo form is accomplished by including in the stain composition a pharmaceutically acceptable oxidizing agent for leuco toluidine blue 0.

The specificity of the toluidine blue 0 cancer delineation test is improved by either the fresh preparation of the stain composition or by pre-application oxidation of any leuco dye present in the composition. Maximum improvement in the specificity of the test is achieved by using both of these procedures.

Accordingly, in one embodiment of the invention, a biological stain composition for in situ delineation for epithelial cancer comprises toluidine blue 0 and a pharmaceutically acceptable oxidizing agent for leuco toluidine blue 0. In another embodiment of the invention, a dry composition for preparing a biological stain for in situ delineation of epithelial cancer comprises toluidine blue 0, a pharmaceutically acceptable oxidizing agent for leuco toluidine blue 0 and an effervescent agent.

In yet another embodiment of the invention a method for preparing a biological stain for in-situ delineation of epithelial cancer comprises the steps of dissolving toluidine blue 0 in a pharmaceutically acceptable solvent and contacting such solution with a pharmaceutically acceptable oxidizing agent for leuco toluidine blue 0.

According to yet another embodiment of the invention a method for preparing a biological stain for in situ delineation of epithelial cancer comprises the steps of preparing a dry composition and then dissolving the dry composition in an aqueous solvent. The dry composition includes toluidine blue 0 and a water soluble, pharmaceutically acceptable oxidizing agent for leuco toluidine blue 0.

In still another embodiment of the invention, a method for delineation of cancer in epithelial tissue comprises the steps of dissolving toluidine blue 0 in a therapeutically acceptable solvent, contacting such solution with a therapeutically acceptable oxidizing agent for leuco toluidine blue 0 and applying such contacted solution to the epithelial tissue in the locus of suspected cancer sites.

In yet another embodiment of the invention useful for delineation of oral cancer, the stain composition contains a flavoring agent and is buffered to prevent degradation of the flavoring.

In yet another embodiment, the invention provides a method for delineation of cancer in oral epithelial tissue which comprises contacting the tissue in the locus of suspected cancerous sites with the flavored buffered composition previously described.

Commercially available toluidine blue 0 is of limited purity and solutions prepared from commercial dye stock may be contaminated with insoluble material. Consequently, in the past, freshly prepared solutions were left to stand for a period of time to allow the insoluble material to precipitate prior to use and to allow for autoxidation of any leuco toluidine blue 0 that might be present in the solution.

Because the stain solutions were infrequently used by typical practitioners, the stability and staining properties of aged dye solutions were suspect. Moreover, preparation of fresh stain compositions was time consuming, increasing the tendency of practitioners to use aged solutions. Further, the pH of such prior solutions tended to vary over the shelf-storage period of the solutions and, when used in the oral cavities of persons with small variations in oral pH, yielded inconsistent clinical results. Finally, due to shelf-storage pH instability, flavoring agents, which are normally susceptible to pH variation, were degraded.

Although fresh compositions can be directly prepared in liquid form, preparation of fresh stain compositions is facilitated by incorporating a pre-selected quantity of toluidine blue 0 powder into an effervescent tablet, formed of components which are highly soluble in a pharmaceutically acceptable solvent, and which, upon disintegration and dissolution of the tablet, react to forth a profusion of gaseous bubbles which aid the dissolution of the dye and the formation of a solution with uniform dye concentration throughout. A quantity of the toluidine blue 0 powder is incorporated into the effervescent tablet which, upon dissolution in a preselected quantity of the solvent, yields the desired final dye concentration in the solution.

The tablet components which cause the effervescent action are selected from among those which are well known in prior art pharmaceutically acceptable effervescent tablet compositions, e.g., so-called pharmaceutical "fusion granulation" mixtures. For example, mixtures of relatively weak organic acids and relatively weak organic bases, which react to form and release carbon dioxide, are suitably employed as well as any other non-toxic, solid, water-soluble compounds which react in or with water with the evolution of gas in sufficient quantity to promote and facilitate mixing and dissolution of the other components of the composition. Obviously, to facilitate oxidation of the leuco form of the toluidine blue 0, the effervescent agents or their reaction products should not act as chemical reducing agents. Typical illustrative examples of suitable effervescent compositions include citric acid/sodium bicarbonate, tartaric acid/potassium carbonate. Other suitable acids include maleic or malic acids. Suitable binders and anti-foaming agents which are known in the art may also be included in the effervescent formulation. Suitable binders may include, for example, polyvinyl pyrrolidone. A suitable anti-foaming agent is dimethyl polysiloxane. Flavoring agents are normally included, if desired.

The formation of carbon dioxide bubbles in the solution will assist in solubilizing the other components, specifically the toluidine blue 0 which has only a limited aqueous solubility and thus a modest dissolution rate. With the incorporation of a solid form of hydrogen peroxide, a form such that upon dissolution in water forms hydrogen peroxide, such as calcium peroxide or urea carbamide (urea peroxide), the hydrogen peroxide will also react with the sodium bicarbonate in a oxidation-reduction reaction with the release of a molecular oxygen. In order to avoid the possible reduction of the toluidine blue 0 in solution, a stoichiometrically adjusted amount of the organic acid, the alkali base (e.g., sodium bicarbonate) and the peroxide must be provided such that an excess of hydrogen peroxide remains in the resulting solution, after the bicarbonate has been exhausted by reaction, so that the toluidine blue 0 remains predominately in the oxidized form, any reduced leuco form of the dye being re-oxidized with the available remaining peroxide concentration.

Oxidizing agents, used to convert any leuco dye in the composition to the chromo form, are selected which are pharmaceutically acceptable, i.e., are non-toxic and do not cause undesired side reactions such as degrading the dye. Those skilled in the art will be able to select and identify suitable oxidizing agents for use in accordance with the invention by routine tests of know non-toxic mild oxidants. For example, according to the presently preferred embodiments of the invention, for directly-prepared liquid compositions it is preferred to use aqueous hydrogen peroxide. For the dry mixtures, e.g., as formulated in effervescent tablets, various solid water soluble "per" compounds, which yield peroxide radicals on dissolution in aqueous solvents, can be employed, such as urea peroxide, sodium perborate tetrahydrate, sodium percarbonate and the like, which form hydrogen peroxide in aqueous solutions. Sufficient peroxide is employed to yield a peroxide concentration in the aqueous final stain composition of about 0.25–1%, to maintain the oxidation state of the dye in the desired chromo form. Other suitable oxidants include sodium perborate, sodium peroxide, sodium periodate, calcium peroxide and the like.

The staining compositions of the invention are preferably formulated to yield a final dye solution which is substantially isotonic and has a pH in the range approximately 2.5 to 7.0, preferably 4.0 to 5.0. This can be accomplished by adding an appropriate liquid buffer system to a liquid formulation or adding solid buffer system to a dry composition. In the case of an effervescent composition a stoichiometric excess of the buffer is employed in order to maintain the proper desired pH of the final aqueous dye composition after dissolution and reaction of the effervescent components.

For example, in a presently preferred embodiment of the invention, a 1% toluidine blue 0 solution is buffered by a 1.0M acetic acid-sodium acetate buffer to a pH of 4.0. Other suitable buffers will be selected by those skilled in the art having regard for this disclosure and by routine tests. For example, other suitable buffers include citric acid-sodium citrate, or mixed acid-salt systems such as citric acid-sodium phosphate and the like. The choice of buffer components and concentrations thereof are determined by the desired pH of the buffered solution as well as by the desired buffer capacity.

The solvent in liquid compositions is an aqueous solvent, according to the preferred embodiment of the invention the solvent includes a pharmaceutically acceptable (i.e., non-toxic, non-reactive) alcohol, e.g., ethanol, to improve penetration of the dye into the epithelial tissue. Such solvents do not appreciably interfere with the tissue staining mechanism and do not themselves contribute to the reduction of chromo toluidine blue 0 to the leuco form of the dye.

In one preferred formulation, the toluidine blue 0 powder is dissolved in a solution of acetic acid, ethanol and water with the addition of hydrogen peroxide in an amount sufficient to maintain the oxidation state of the toluidine blue 0 in the chromo form. Flavoring, stable to hydrogen peroxide, is be added to the formulation to enhance the palatability of the dye rinse solution. For use other than as an oral dye rinse solution, the flavoring can be omitted from the formation.

When it is desired that the toluidine blue 0 be available in a simple, convenient single use form, all critical components of the dye rinse solution can be prepared as a dry powdered mixture to be used directly or to be combined with other ingredients to provide for a rapidly dissolving tablet. The powder mixture or tablet can then be packaged in a convenient container for mixing and dissolution with water and/or other solvents such as water and ethanol.

The present invention also encompasses formulating an effervescent powder or tablet mixture to contain an oxidizing agent to offset any potential reduction of the dye to the leuco form when dissolved in solution. This can be accomplished in a number of ways which are obvious to those skilled in the art. For example all of the composition components can be formulated in a single tablet. Alternatively, the oxidizing agent and dye can be formulated in separate tablets both of which are added to the aqueous solvent to form the final stain composition.

The amount of dye in the dry or liquid formulations is preferably adjusted to yield a toluidine blue concentration of approximately 1% by weight in the final stain composition, although higher concentrations can be employed and lower concentrations are at least partially effective, e.g., from about 0.5 to about 3.5 wt. %.

WORKING EXAMPLES

The following examples are presented to illustrate the practice of the invention and the presently known best modes of the practice thereof. These examples are for illustrative examples only and are not intended to indicate limits on the scope of the invention.

EXAMPLE I

This example illustrates the preparation of a fresh dye solution from separate liquid and solid components. The following components are mixed.

| | |
|---|---|
| 20 grams | toluidine blue 0 (purified) |
| 200 ml | acetic acid, U.S.P. |
| 168 ml | ethanol, U.S.P. |
| 14.28 ml | hydrogen peroxide, 35% U.S.P. |
| 3 ml | flavoring (e.g., grape) |
| 1614 ml | purified $H_2O$, U.P.S., Q.S. to 2000 ml final volume |

EXAMPLE II

This example illustrates the preparation of a fresh dye solution from premixed solid components which are thereafter dissolved in water.

The following dry components are intimately admixed.

| | |
|---|---|
| toluidine blue O | 24 parts |
| citric acid | 48 parts |
| sodium citrate | 30 parts |
| urea carbamide | 6 parts |

This dry mixture can be stored for extended periods of time and a freshly prepared dye solution can be prepared just prior to use by dissolving a sufficient weight of this mixture in water to yield a final toluidine blue 0 concentration of 1% by weight.

EXAMPLE III

This example illustrates a procedure in which the components of a final dye composition are combined in two separate tablets, one containing the oxidizing agent and another containing the remaining components.

| Tablet A | |
|---|---|
| | Wt. % |
| sodium perborate | 20.0 |
| sorbitol | 77.8 |
| polyethylene glycol | 2.0 |
| siloxane polymer | 0.2 |

| Tablet B | |
|---|---|
| | Wt. % |
| citric acid | 35.0 |
| $NaHCO_2$ | 25.0 |
| toluidine blue O | 20.0 |
| cationic surfactant | 3.0 |
| flavor | 3.0 |
| sweetener | 2.0 |
| sorbitol | 8.0 |
| polyethylene glycol | 2.0 |
| sodium benzoate | 1.8 |
| siloxane polymer | 0.2 |

Tablet A and tablet B are packaged together in a sealed disposable container. The final dye formulation is made up in the container with the addition of water or water-ethanol to yield a final dye content of approximately 1 wt. %.

EXAMPLE IV

This example illustrates the preparation of a single tablet formulation.

|  | Wt. % |
| --- | --- |
| citric acid | 35.0 |
| NaHCO$_2$ | 25.0 |
| toluidine blue O | 20.0 |
| cationic surfactant | 3.0 |
| flavor | 3.0 |
| sweetener | 2.0 |
| urea peroxide | 8.0 |
| polyethylene glycol | 2.0 |
| sodium benzoate | 1.8 |
| siloxane polymer | 0.2 |

In Examples III and IV the sorbitol, glycol and siloxane polymers are included as tableting aids. Preservatives and antimicrobial agents such as sodium benzoate may also be added. Sweeteners and flavors which are well known in the mouth wash art may also be employed as optional additives.

EXAMPLE V

This example describes the presently preferred formulation embodying the principles of the present invention:

| toluidine blue O | 10.00 grams |
| --- | --- |
| glacial acetic acid | 43.75 ml |
| sodium acetate trihydrate | 24.50 grams |
| SD alcohol (95% Ethyl alcohol) | 42.00 ml |
| Hydrogen peroxide (30%) | 3.70 ml |
| Dragoco grape flavor | 2.00 ml |
| Purified Water | 908.60 ml |

The ingredients of this formulation are mixed to yield 1000 ml of a 1% toluidine blue O solution with pH of 4.0, buffered by 1.0M acetic acid-acetate buffer.

EXAMPLE VI

The example illustrates the preferred practice of the cancer detection method of the invention, using the formulation of Example V for purposes of illustration:

The patient is instructed to first rinse the oral cavity with approximately 10 ml. of water for approximately 30 seconds to remove loose debris and expectorates.

The patient then rinses the mouth with approximately 10 ml of 1% acetic acid for approximately 30 seconds to remove excess saliva.

Using a cotton applicator saturated with the composition of Example V, the dye composition is applied directly to a lesion site and the surrounding tissue. The dye composition remains on the application site for about 30-60 seconds.

The patient then rinses the mouth with approximately 10 ml of 1% acetic acid for about 30 seconds to remove excess dye and, finally, rinses the mouth with approximately 10 ml of water.

Observation of the staining pattern reveals the presence of any cancerous tissue.

To detect possible cancerous tissue throughout the mouth, the patient can rinse the entire oral cavity for about 30 seconds using about 10 ml of the composition of Example V, instead of applying the dye composition to specific sites with the cotton applicator. Otherwise, the procedure for such a general rinse is the same as described above.

Having described our invention in such terms as to enable those skilled in the art to understand and practice it, and having disclosed the presently preferred embodiment thereof, we claim:

1. A biological stain composition for in-situ delineation of epithelial cancer, comprising:
   (a) toluidine blue 0; and
   (b) a pharmaceutically acceptable oxidizing agent for leuco toluidine blue 0.

2. A dry composition for preparing a biological stain for in-situ delineation of epithelial cancer, comprising:
   (a) toluidine blue 0;
   (b) a pharmaceutically acceptable oxidizing agent for leuco toluidine blue 0; and
   (c) an effervescent agent.

3. A method for preparing a biological composition stain for in-situ delineation of epithelial cancer, comprising:
   (a) dissolving toluidine blue 0 in a pharmaceutically acceptable solvent; and
   (b) contacting such solution with a pharmaceutically acceptable oxidizing agent for leuco toluidine blue 0.

4. A method for preparing an aqueous biological stain composition for in-situ delineation of epithelial cancer, comprising:
   (a) preparing a dry composition including;
      (i) toluidine blue 0,
      (ii) a water-soluble, pharmaceutically acceptable oxidizing agent for leuco toluidine blue 0, and
      (iii) an effervescent agent; and
   (b) dissolving said dry composition in an aqueous solvent.

5. A method for delineation of epithelial cancer in epithelial tissue, comprising;
   (a) dissolving toluidine blue 0 in a pharmaceutically acceptable solvent;
   (b) contacting such solution with a pharmaceutically acceptable oxidizing agent for leuco toluidine blue 0; and
   (c) applying such contacted solution to said epithelial tissue in the locus of suspected cancer sites.

6. The composition of claim 1 which further includes a buffering agent to maintain the pH in the range 2.5–7.0.

7. The composition of claim 6 in which the pH is maintained in the range 3.5–5.0.

8. The composition of claim 6, further including a flavoring agent.

9. A biological stain composition for in-situ detection of epithelial cancer, comprising:
   (a) toluidine blue 0;
   (b) hydrogen peroxide, in a minor amount effective to maintain said toluidine blue 0 in chromo form;
   (c) aqueous ethanol solvent carrier;
   (d) a flavoring agent soluble in said carrier; and
   (e) a buffering agent system to maintain the pH of said composition in the range 3.5–5.0.

10. A method for delineation of cancer in oral epithelial tissue, comprising contacting said tissue in the locus of suspected cancerous sites with the composition of claim 9.

* * * * *